United States Patent [19]

Kiezulas

[11] Patent Number: 5,026,607
[45] Date of Patent: Jun. 25, 1991

[54] MEDICAL APPARATUS HAVING PROTECTIVE, LUBRICIOUS COATING

[75] Inventor: Margaret P. Kiezulas, Carlisle, Mass.

[73] Assignee: C. R. Bard, Inc., Murray Hill, N.J.

[21] Appl. No.: 370,917

[22] Filed: Jun. 23, 1989

[51] Int. Cl.$^5$ .................. B32B 27/00; B32B 27/40
[52] U.S. Cl. ........................... 428/423.7; 427/2; 428/423.1; 428/447; 604/96; 604/265; 606/194
[58] Field of Search .................. 427/2; 428/447, 423.1, 428/423.7; 606/96, 194; 604/265

[56] References Cited

U.S. PATENT DOCUMENTS

| | | | |
|---|---|---|---|
| 4,011,189 | 3/1977 | Keil | 252/12 X |
| 4,263,188 | 4/1981 | Hampton et al. | 427/128 X |
| 4,301,053 | 11/1981 | Wolfrey | 428/412 X |
| 4,306,998 | 12/1981 | Wenzel et al. | 528/48 X |
| 4,598,120 | 7/1986 | Thoma et al. | 524/591 |
| 4,605,698 | 8/1986 | Briden | 524/559 |
| 4,642,267 | 2/1987 | Creasy et al. | 428/413 |
| 4,666,437 | 5/1987 | Lambert | 427/2 X |
| 4,675,361 | 6/1987 | Ward, Jr. | 525/92 |
| 4,739,013 | 4/1988 | Pinchuk | 264/331.19 X |
| 4,769,030 | 9/1988 | Pinchuk | 427/2 X |
| 4,851,009 | 7/1989 | Pinchuk | 427/2 X |

Primary Examiner—Michael Lusignan
Attorney, Agent, or Firm—Wolf, Greenfield & Sacks

[57] ABSTRACT

A method for providing a medical apparatus with a protective, lubricious coating is described. The method comprises providing a coating solution which contains a protective compound such as a urethane, a slip additive such as a siloxane, and optionally, a crosslinking agent for the protective compound such as a polyfunctional aziridine, coating the solution onto a surface of a medical apparatus and allowing the coating to set. The resulting surface coating is lubricious, tough and flexible. The coating is well suited for use with materials used as components of balloon catheters.

32 Claims, No Drawings

MEDICAL APPARATUS HAVING PROTECTIVE, LUBRICIOUS COATING

BACKGROUND OF THE INVENTION

In coronary angioplasty and related technologies, a catheter having an inflatable balloon attached at the catheter's distal end is employed. Such balloons have been known to fail by damage resulting from abrasion and puncture during handling and use and also from over-inflation. Additionally, the balloons and catheters upon which they are mounted generally have a higher coefficient of friction than desired for ease of use. Thus, it often becomes difficult to guide the catheter into a desired location in a patient due to friction between the apparatus and the vessel through which the apparatus passes.

A variety of urethane based coating compositions for medical applications are known in the art. For example, U.S. Pat. No. 4,642,267 to Creasy et al. describes hydrophilic polymer blends useful for coating catheters and other surfaces. The coating comprises a thermoplastic polyurethane and a hydrophilic poly (N-vinyl lactam) such as polyvinylpyrrolidone. Additional components such as crosslinking agents and wax dispersions can be added to the blend. U.S Pat. No. 4,675,361 to Ward, Jr. relates to polymer systems useful for coating surfaces having blood and tissue contacting applications. The system comprises a base polymer, such as a polyurethane, containing at least one polymer additive comprising a segmented block copolymer having both hard and soft segments.

Although each of these patents describes an application involving biomedical apparatus, a need still exists for a simple, easy-to apply coating which is biocompatible, lubricious and provides a protective layer to the surface upon which it is applied.

SUMMARY OF THE INVENTION

In a broad sense, the present invention comprises medical apparatus having a coating which comprises a protective compound and a slip additive. The protective compound serves to protect the surface upon which it is coated and to provide a network to contain the slip additive. Urethanes are particularly desirable as the protective compound due to their protective qualities and water-based urethanes are especially preferred due to their ability to provide a carboxyl functionality to the coating. Carboxyl functionality allows crosslinking of the coating with carboxyl groups present on the surface of the apparatus to bind the coating to the surface and also allows crosslinking within the urethane itself to provide added strength and toughness to the coating.

The coating is formed on a surface by a method which comprises providing a coating solution having between about 2% and about 80% solids, preferably between about 15% and about 25% solids, and which contains the protective compound, the slip additive, and optionally, a crosslinking agent for the protective compound; the solution is applied to a surface using any of a variety of methods for surface coating, and the coating is allowed to set into a protective, lubricious layer upon the apparatus surface.

In a preferred embodiment, the protective compound is a urethane, the slip additive is a dimethyl siloxane, and the crosslinking agent for the urethane is a polyfunctional aziridine.

The coating and method is particularly well suited for use on materials such as polyetheylene terephthalate (PET), a polymeric material having many properties which render it desirable for use as an angioplasty balloon.

DETAILED DESCRIPTION OF THE INVENTION

As used herein, the term "medical apparatus" means apparatus suited for use in medical applications, particularly in in vivo applications. Such apparatus specifically includes, but is not limited to, balloons, catheters, guidewires, stylets and introducers. Of particular note for use with the invention are catheters having inflatable balloons such as those developed for use in angioplasty and valvuloplasty, guide catheters and guidewires.

As used herein the term "slip additive" means a chemical compound capable of being included in a protective network to impart a lower coefficient of friction to the network surface. Such compounds include but are not limited to silicon-based compounds such as silicones and siloxanes, fluorochemicals such as polytetrafluoroethylene (PTFE), and a variety of waxes.

In a preferred embodiment, the coating is provided in the form of a solution having a solids content of between about 15% and about 25% and which comprises a water-based urethane dispersion, a dimethyl siloxane emulsion containing at least about 15% solids and a polyfunctional aziridine. Unless otherwise noted, all percentages described herein are percentages by weight. Other materials, such as pigments and radioopaque compounds can be added as well.

A high molecular weight, hard, non-yellowing, water-based urethane is preferred as the resin of the coating. Particularly preferred is a urethane dispersion having a solids content of between about 30% and about 50% in a solution comprising a mixture of water, N-Methyl-2-pyrrolidone (CAS#872-50-4) and triethylamine (CAS#121-44-8). Such a dispersion is available from Permuthane (Peabody, Mass.) as UE41-222. It is particularly desirable that the protective compound be dispersed in a liquid which will not harm the surface upon which the coating is applied. Thus, for a surface such as a PET balloon, the urethane is preferably provided as a dispersion in an aqueous medium.

The slip additive is preferably an emulsion of an industrial grade dimethyl siloxane in water having a siloxane content of at least about 15%. While a slip additive having up to about 100% siloxane or silicone can be used, an aqueous emulsion of the material diluted to about 15% solids is easier to handle during mixing of the coating solution. A preferred dimethyl siloxane is available from Dow Corning Corporation (Midland, Mich.) as Q2-3238. This is available neat and can be subsequently combined with water to form an emulsion having approximately 15% dimethyl siloxane.

When used in a urethane-based coating, the crosslinking agent is preferably a polyfunctional aziridine. Although this material can be diluted prior to use, it is preferably used neat to minimize further dilution of the coating solution. Most preferred is the material available from Permuthane (Peabody, Mass.) as KM10-1703. This material will hydrolyze in water or humid air and reacts rapidly with acids. Once added to the coating solution, application should be within about 48 hours if room temperature conditions are maintained. Increased temperature will cause increased hydrolysis, inactivity of the material and promotion of crosslinking of the coating, resulting in a higher coating viscosity. Since the aziridine component is caustic, it must be fully reacted or hydrolyzed before the coated medical apparatus is suitable for in vivo use.

A most preferred coating formulation has a solids content of approximately 17% upon application and comprises a mixture containing approximately 42.55% UE41-222 urethane dispersion, 12.77% Q2-3238 siloxane dispersion, 2.13% KM10-1703 polyfunctional aziridine and 42.55% distilled water. The formulation can be made by mixing the siloxane emulsion with the distilled water and subsequently adding the urethane dispersion. This is then mixed in a capped glass container with a magnetic stirrer until all parts are thoroughly mixed. The crosslinking agent is subsequently added to the solution just prior to application of the coating upon a surface. The addition of the crosslinking agent just prior to application of the coating prevents the urethane from crosslinking only with itself and thereby allows a sufficient carboxyl group density within the coating for crosslinking with the surface to be coated.

The material can be applied to surfaces using any of a variety of methods. Preferred among these are dipping, spray coating, rolling and brushing. Subsequent to the actual coating step, the coated devices are allowed to cure. The curing is preferably carried out by placing the coated devices in an oven at approximately 50° C. until the urethane is fully crosslinked.

The resulting coating is flexible, durable and lubricious, retaining its lubricity for an extended period of time. These properties are a direct result of the protective compound's ability to act as a binder to maintain domains of the slip additive. Thus the durable binder enhances lubricity by preventing the removal of the slip additive from the substrate surface. Additionally, the protective compound provides an abrasion resistance to the substrate surface, thereby minimizing the effect of abuse on the device.

In the case of PET balloons, the abrasion resistance provided by the coating is particularly desirable since it substantially reduces damage to the balloon surface. This decreases the likelihood of balloon failure caused by mishandling during balloon preparation or use.

In the case of urethane-based coatings, bonding of the coating to the substrate surface upon which it is applied can be achieved by a crosslinking reaction between carboxyl functional groups present in the urethane and carboxyl functional groups present on the substrate surface. One method by which such bonding can be achieved involves a crosslinking reaction utilizing the aforementioned polyfunctional aziridine through which the linkage will occur.

In a most preferred application, the coating solution is intended to be used to provide a flexible, protective and lubricious coating to the surface of angioplasty balloons. These balloons can be made of a variety of materials such as polyvinyl chloride and polyethylene, although polyethylene terephthalate (PET) is preferred. Unfortunately, PET lacks the requisite density of available carboxyl groups to provide for satisfactory bonding of the urethane-based coating with the surface. Therefore, it is often desirable to provide a first layer of a primer material between the PET balloon surface and the coating.

A preferred primer is a dispersion containing an ethylene acrylic acid (EAA) resin. A preferred EAA resin such as Primacor 5980 available from Dow-Corning Corporation (Midland, Mich.) can be mixed in an aqueous solution to provide a formulation containing approximately 25% solids. As with the topcoat formulation, the EAA resin must be applied from a solvent which will not damage the surface of the apparatus to be coated. When applying the primer to a PET balloon, the EAA should be dissolved in an aqueous solvent. Since EAA resin has a very low solubility in water, it is necessary to first convert the EAA into a soluble salt. This can be accomplished by combining the resin with a quantity of ammonia sufficient to neutralize the carboxyl groups contained therein.

The required amount of ammonia is added to a volume of water into which a sufficient quantity of EAA has been mixed to form a dispersion. The container into which the components have been poured is then sealed and heated to approximately 110° C. for between about 15 and 30 minutes. The solution is then allowed to cool at which point it is ready for use. It should be noted that during the mixing steps, it is desirable to use a condenser to prevent evaporation of any of the components prior to sealing the mixing vessel.

As with the topcoat solution, the primer can be applied to the substrate surface using a wide variety of methods including, but not limited to, dipping, spray coating, rolling and brushing. Once applied, the primer should be cured until completely dry. Heat curing at approximately 50° C. has been found to be satisfactory for the EAA primer described previously. Subsequently, the topcoat solution can be applied to the primer-coated device surface using the method previously described.

As an alternative to the use of a primer, a surface functionality can be obtained on the substrate surface using a variety of other techniques. For example, surface functionality can be obtained using a plasma or corona discharge or by exposing the surface to a flame. In the case of plasma or corona discharge, the functionality obtained on the surface can be tailored through the use of process atmosphere variation. Thus, when an oxygen derived functionality (i.e. —OH or —COOH) is desired, the surface can be plasma treated in an oxygen-containing atmosphere. Alternatively, if an amine functionality is preferred, the treating process can be carried out in a nitrogen-containing atmosphere.

When the surface to be coated comprises a catheter-mounted balloon, it is preferred that the balloon be inflated prior to applying the primer and/or topcoat. This allows the formation of a coating layer having a generally uniform thickness and also prevents adhesion between balloon surfaces that may contact one another in the deflated state. Care should be taken to ensure that no primer or topcoat is allowed to remain within any open lumen of the catheter as this will likely cause undesirable lumen blockages. Blotting the catheter end and any exposed lumen ports with a suitable blotting material subsequent to applying the layer will prevent such blockages. Alternatively, the catheter lumens can be purged using air or an inert gas.

Since the preferred topcoat solution contains both a slip additive and a crosslinker for the protective compound, the solution can be applied to surfaces having adequate functional group density in a single pass. This provides a process efficiency, as it eliminates the need to carry out a crosslinking step subsequent to application of the coating to the substrate surface.

When applied to the surface of PET balloons, the coating described herein has resulted in enhanced scratch resistance and a decreased coefficient of friction without noticeably altering the balloon profile or flexibility.

It should be noted that although the preferred coating formulation described herein contains a water-based urethane resin and a polyfunctional aziridine crosslinking agent, the invention is not intended to be limited thereto. Rather, the invention is intended to apply to medical apparatus having protective and lubricious coatings provided by a protective resin system containing a slip additive, and, optionally, any of a variety of crosslinking agents selected to be compatible with the coating and the surface on which the coating is to be applied. For example, resin systems including but not limited to acrylics, vinylidine chlorides and vinyls can be used as the protective compound and formaldehyde derivatives (melamine, urea, etc.), isocyanates, and carbodiimides are examples of other materials which can be used as crosslinking agents. In still another embodiment, a urethane resin can be used in combination with a fluorochemical resin which acts as both a binder and a slip additive. Preferred fluorochemicals are marketed as FC-10 available from 3M Company and Lumiflon available from ICI Corporation. Such systems can be crosslinked using isocyanates.

EXAMPLE

A coating solution prepared in accordance with the teachings of this invention and having the following formulation was provided:

| Component | Supplier/Designation | Weight % |
|---|---|---|
| Urethane | Permuthane/UE41-222 | 42.55 |
| Dimethyl Siloxane | Dow/Q2-3238 | 12.77 |
| Aziridine | Permuthane/KM10-1703 | 2.13 |
| Water | — | 42.55 |

The coating solution was applied to a balloon catheter having a 3.0×20 mm PET balloon bonded to the catheter with a UV-activated adhesive, by dipping the inflated catheter into a volume of the coating mixture. Subsequent to the dipping, the coated apparatus was heat cured at approximately 50° C. until dry and then sterilized using ethylene oxide. Testing of the catheter was carried out using an uncoated balloon catheter as a control.

The two catheters were individually passed through an 8F (0.072") channel having a curvature replicating that of the final curve of an FL4 guide catheter. A 0.14" PTFE-coated guidewire was used. The force of pushing and pulling the catheter was measured for different insertion lengths and the average minimum and maximum forces (in grams) for 10 cycles of both pushing and pulling of the coated and uncoated catheters were determined. The results of this test are summarized below:

| Sample | Push (min.) | Push (max.) | Pull (min.) | Pull (max.) |
|---|---|---|---|---|
| Coated | 11.0 | 32.5 | 8.4 | 25.4 |
| Uncoated | 20.5 | 42.5 | 16.7 | 33.0 |
| % Improvement Coated v. Uncoated | 46% | 21% | 50% | 23% |

As evidenced by the above, the coated catheter displayed a lower resistance to both pushing and pulling through the channel. This reduced resistance represented an average improvement of approximately 34% overall when comparing the coated catheter to the uncoated control catheter.

What is claimed is:

1. A method for providing a protective, lubricious coating on surfaces of medical apparatus, the method comprising:
    a) providing a coating solution having a solids content of between about 2% and about 80% by weight, the coating solution comprising an aqueous dispersion of a urethane having a solids content of between about 30% and about 50%, and a silicone or siloxane emulsion having a solids content of at least about 15%;
    b) applying the coating solution to a surface of the medical apparatus; and,
    c) allowing the coating to set into a layer upon the apparatus surface.

2. A method as in claim 1 wherein the coating solution additionally contains a crosslinking agent for the urethane.

3. A method as in claim 2 wherein the crosslinking agent comprises a polyfunctional aziridine.

4. A method as in claim 1 wherein the coating is applied to a polyethylene terephthalate surface.

5. A method as in claim 4 wherein a primer is applied to the surface prior to applying the coating.

6. A method as in claim 5 wherein the primer comprises ethylene acrylic acid.

7. A method as in claim 1 wherein the urethane is dispersed in an aqueous solution containing triethylamine and N-methyl-2-pyrrolidone.

8. A method as in claim 1 wherein the siloxane is provided as an emulsion of dimethyl siloxane.

9. A method as in claim 8 wherein the emulsion contains a solids content of about 17%.

10. A method as in claim 1 wherein the coating solution contains between about 15% and about 25% solids by weight.

11. A method as in claim 1 wherein the medical apparatus comprises a balloon.

12. A method as in claim 1 wherein the apparatus comprises a catheter.

13. A method as in claim 1 wherein the apparatus comprises a guidewire.

14. A medical apparatus having a protective, lubricious surface coating, the coating comprising a crosslinked, water-based urethane compound having domains of a silicone or siloxane slip additive dispersed therethrough.

15. An apparatus as in claim 14 wherein the slip additive comprises dimethyl siloxane.

16. An apparatus as in claim 14 wherein the surface upon which the coating is applied comprises polyethylene terephthalate.

17. An apparatus as in claim 16 which comprises a balloon.

18. An apparatus as in claim 14 which comprises a catheter.

19. An apparatus as in claim 14 which comprises a guidewire.

20. An apparatus as in claim 14 having a primer layer disposed between the coating and the surface.

21. An apparatus as in claim 20 wherein the primer layer has a functionality suitable for crosslinking with the coating.

22. An apparatus as in claim 21 wherein the primer layer has a carboxyl functionality.

23. An apparatus as in claim 22 wherein the primer layer comprises ethylene acrylic acid.

24. An apparatus as in claim 14 wherein the coating additionally comprises a crosslinking agent for the urethane.

25. An apparatus as in claim 24 wherein the crosslinking agent comprises a polyfunctional aziridine.

26. An article of manufacture comprising a medical device having a protective, lubricious coating on a surface thereof, the coating provided by the method comprising:
   a) providing a coating solution having a solids content of between about 2% and about 80% by weight, the coating solution comprising an aqueous dispersion of a urethane having a solids content of between about 30% and about 50%, and a silicone or siloxane emulsion having a solids content of at least about 15%;
   b) applying the coating solution to a surface of the medical device; and,
   c) allowing the coating to set into a layer upon the device surface.

27. The article of claim 26 wherein the coating solution additionally contains a crosslinking agent for the urethane.

28. The article of claim 27 wherein the crosslinking agent comprises a polyfunctional aziridine.

29. The article of claim 26 wherein the coating is applied to a polyethylene terephthalate surface.

30. The article of claim 29 wherein a primer is applied to the surface prior to applying the coating.

31. The article of claim 30 wherein the primer comprises ethylene acrylic acid.

32. The article of claim 26 wherein the medical device is selected from the group consisting of balloons, catheters and guidewires.

* * * * *